United States Patent [19]

Kapicak et al.

[11] Patent Number: 4,616,093

[45] Date of Patent: Oct. 7, 1986

[54] PROCESS FOR PREPARING A DIESTER OF OXALIC ACID IN THE VAPOR PHASE

[75] Inventors: Louis A. Kapicak, Charleston; Joseph P. Henry, South Charleston, both of W. Va.

[73] Assignee: Union Carbide Corporation, Danbury, Conn.

[21] Appl. No.: 239,762

[22] Filed: Mar. 12, 1981

Related U.S. Application Data

[63] Continuation-in-part of Ser. No. 227,640, Jan. 23, 1981, abandoned.

[51] Int. Cl.$^4$ .............................................. C07C 67/36
[52] U.S. Cl. .................................. 560/204; 502/152; 502/327; 560/190
[58] Field of Search ........................ 560/204; 252/472

[56] References Cited

U.S. PATENT DOCUMENTS 4,138,587  2/1979  Yamasaki et al. ................... 560/204
4,229,591  10/1980  Nishimura et al. ................. 560/204

*Primary Examiner*—Natalie Trousof
*Assistant Examiner*—Vera C. Clarke
*Attorney, Agent, or Firm*—Steven T. Trinker

[57] ABSTRACT

A process is disclosed for preparing a diester of oxalic acid by contacting carbon monoxide and an ester of nitrous acid in the vapor state under a pressure in the presence of a special palladium supported catalyst.

1 Claim, No Drawings

PROCESS FOR PREPARING A DIESTER OF OXALIC ACID IN THE VAPOR PHASE

FIELD OF THE INVENTION

This invention relates to a novel process for preparing diesters of oxalic acid. More particularly, this invention relates to a process for preparing a diester of oxalic acid which comprises contacting carbon monoxide with an ester of nitrous acid under a pressure in the presence of a palladium catalyst supported on a non-acidic carrier having a low surface area.

BACKGROUND OF THE INVENTION

The preparation of diesters of oxalic acid (oxalates) is of particular interest to the chemical industry owing to the varied uses of these compounds. Not only may these diesters serve to act as the starting materials for such important compounds as oxalic acid, oxamide or ethylene glycol but they may also find extensive use as intermediates for dyes, pharmaceuticals, and the like.

Prior to the instant invention, there have been proposed numerous processes for the preparation of diesters of oxalic acid employing various catalysts, cocatalysts, reaction accelerators, and the like, for use in a liquid phase reaction to make oxalates. However, these conventional processes suffer from significant by-product formation as would be expected from the conventional liquid phase processes.

A particularly interesting attempt to prepare diesters of oxalic acid in the liquid phase is disclosed in U.S. Pat. No. 4,138,587. This patent employs nitric acid or a nitrogen oxide as an accelerator in the presence of a solid platinum group metal or salt, thereof, molecular oxygen, an alcohol and carbon monoxide to produce the diester of oxalic acid. Unfortunately, the process is a liquid phase process and suffers in several significant practical aspects, such as catalyst losses by virtue of dissolution, large by-product formation, low efficiencies to product, to name a few.

U.S. Pat. No. 4,229,591 discloses a vapor phase process. The process disclosed in the patent involves contacting an ester of nitrous acid with carbon monoxide in the gaseous phase under normal pressure in the presence of a solid catalyst containing metallic palladium or a salt thereof at a temperature of 50° to 200° C., the ester of nitrous acid being nitrous acid ester of an alcohol having 1 to 8 carbon atoms.

Although this above-described process is advantageous as compared to liquid phase processes the process fails to distinguish the role played by the carrier for the catalysts employed in such a heterogeneous vapor phase process. This is better shown by reference to the example of the patent. Examples 1 to 24 depict various palladium catalysts but in each case the carrier for the palladium catalyst was either carbon or $SiO_2$. The specification refers also to alumina, diatomaceous earth, pumice, zeolite, and molecular sieves. Obviously, the broad general listing of carriers fails to signify any advantage of one carrier over another. Carbon and silica ($SiO_2$) carriers are acidic carriers with high surface areas (much greater than 10 $m^2/g$). For example, the patent mentions "alumina" as a carrier, and this encompasses a wide variety of materials ranging from high surface area acidic-alumina (gamma-alumina), fibrous alumina, to alpha-alumina.

SUMMARY OF THE INVENTION

The invention comprises a vapor phase, heterogeneous process for preparing a diester of oxalic nitrous acid with carbon monoxide in the vapor state under a pressure in the presence of a solid palladium supported catalyst comprising metallic palladium or a salt thereof deposited on a non-acidic carrier having a low surface area at a temperature of from about 50° C. to about 200° C. There is recovered a dialkyl oxalate in which the alkyl moiety corresponds to the alcohol used in making the ester of nitrous acid.

DETAILED DESCRIPTION OF THE INVENTION

It has been found that by employing a palladium catalyst deposited on a non-acidic carrier having a low surface area, (e.g., less than about 10 $m^2/g$), in the formation of diesters of oxalic acid (i.e. oxalate process) from nitrous acid esters and carbon monoxide in the vapor phase that several advantages may be obtained, such as increased conversion to the diester product, longer catalyst life, less by-product formation, and lower palladium content is required. (The terms "vapor state" and "vapor phase" are equivalent in their use herein.)

The esters of nitrous acid which are employed in the process may be formed by conventional synthetic schemes or may be provided in the form of a nitrogen compound which in situ may provide by reaction with an alcohol, as described herein, an ester of nitrous acid in the reaction system.

Exemplary of nitrogen compounds which can be used to make nitrous acid esters or can be employed to form the ester in situ are nitrogen monoxide, nitrogen dioxide, dinitrogen trioxide, dinitrogen tetraoxide, and hydrates thereof. In the case where nitrogen monoxide is employed it is necessary to employ molecular oxygen therewith to form the requisite nitrogen compound.

The preferred esters of nitrous acid are esters derived from saturated monohydric aliphatic alcohols to form alkyl nitrite, such as those formed from a saturated monohydric open-chain aliphatic alcohol having 1 to 8 carbon atoms or an alicyclic alcohol having 1 to 8 carbon atoms. The most preferred esters of nitrous acid are those prepared from methanol and ethanol. As the alcohol component may be mentioned aliphatic alcohols such as methanol, ethanol, n-propanol, isopropanol, n-butanol, isobutanol, sec-butanol, tert-butanol, n-amyl alcohol, isoamyl alcohol, hexanol, octanol, etc., and alicyclic alcohols such as cyclohexanol, methylcyclohexanol, etc. These alcohols may contain therein a substituent such as an alkoxy group which does not inhibit the reaction.

The process by which the ester of nitrous acid is prepared is not narrowly critical so long as the ester of nitrous acid does not contain deletereous components, such as nitric acid, which may adversely affect the palladium catalyst. A preferred and highly advantageous process for preparing the methyl and ethyl esters of nitrous acid is disclosed in co-pending U.S. Ser. Nos. 238,176, filed January 23, 1981 and (239,761 filed 3/12/81 now Pat. No. 4,353,843) to Arthur Doumaux et al wherein a novel vapor phase process for the preparation of methyl and ethyl nitrite is provided. The disclosure of these applications is incorporated by reference herein.

The aforementioned esters of nitrous acid are employed in the instant process reaction with carbon monoxide which may be obtained from any conventional source. It may be pure, contain small amounts of hydrogen, and/or it may be diluted with an inert gaseous diluent such as nitrogen, carbon dioxide and the like. The concentration of carbon monoxide, in the reaction zone is not narrowly critical and may vary over a wide range between about 1 and about 99 percent by volume. Typically, the concentration of carbon monoxide is in the range of between about 10 percent and about 95 percent by volume, wherein the actual concentration of carbon monoxide in the reaction mixture will depend on the alkyl nitrite employed and its concentration, the catalyst employed in the process, concentration of inert gaseous diluent and the selected process conditions.

It may be preferable to carry out the oxalate process in the presence of an inert gaseous diluent to moderate the reaction to preclude the formation of explosive mixtures and prevent the formation of excessive amounts of undesirable by-products. The inert gaseous diluent may be added with the alkyl nitrite should it not have been employed in making the nitrite. As the inert diluent, it is preferred to employ nitrogen, carbon dioxide or other inert gaseous compounds. The use of carbon dioxide may be preferred since it provides a higher heat capacity as compared to nitrogen. The inert gaseous diluent is employed in sufficient amount to provide the aforementioned objectives. The inert gaseous diluent may be employed in the process such that between about 0 (zero) and about 99 percent by volume comprises inert gaseous diluent. Typically, the concentration of inert gaseous diluent is between about 1 percent and about 90 percent by volume wherein the actual concentration employed is chosen as before discussed with respect to the concentration of carbon monoxide.

The oxalate process is generally carried out at a temperature between about 50° C. and about 200° C. and preferably between about 75° C. and about 150° C.

The reaction pressure is generally atmospheric (14.7 psia) or superatmospheric pressure such that the pressure is between about 1 atmosphere (14.7 psia) and about 7 atmospheres and most preferably between about 1 atmosphere and about 4 atmospheres. If desired, subatmospheric pressure may be employed.

The vapor state reaction for the formation of the diesters of oxalic acid is preferably carried out by providing an oxalate forming reaction zone which is without deleterious amounts of water. While some amount of water may be tolerated the amount of water formed in the nitrous ester forming reaction zone is deleterious and a sufficient amount of said water is preferably removed prior to introduction into the oxalate forming reaction zone. This may be accomplished by use of a water condensor (such as a vapor-liquid separator) after alkyl nitrite formation or by the use of some other dehydration process. The amount of water which is deleterious to the vapor state reaction for the formation of diesters of oxalic acid is determined, in part, by the selection of ester of nitrous acid, temperature, pressure, etc. In general, a deleterious amount of water is that amount of water which causes a significant change in the rate of oxalate formed as compared to the rate when a non-deleterious amount is present. The amount of water in the oxalate forming reaction zone is preferably less than about 5.0 percent by volume, based on the total reaction volume, more preferably less than about 2.0 percent by volume and most preferably less than about 1.0 percent by volume.

The process is preferably carried out in a tubular reactor with fixed catalyst bed or dynamic bed, such as a fluidized catalyst bed. The particulate catalyst may be diluted with particles of an inert carrier or other inert materials, to enhance control over the reaction temperature.

The contact or residence time during which the process occurs is generally less than about 30 seconds and preferably between about 0.05 and about 10 seconds although longer or shorter residence times may be employed.

CATALYST

In general terms, the special catalysts employed in this process are metallic palladium or salts thereof deposited on a non-acidic carrier having a low surface area. By "non-acidic" it is meant that the carrier is not of the type that has an acid character due to acid moieties. Particulate alpha-alumina is exemplary of such a non-acidic carrier having low surface area.

The catalyst carrier may be selected from conventional, porous, refractory materials which are essentially inert to the reactant and products at reaction conditions. These materials are generally labelled as "macroporous" and consist of porous materials having low surface area of less than about 10 square meters per gram of carrier and preferably less than about 5 square meters per gram. The surface area is measured by the conventional B.E.T. method described by Brunauer, S., Emmet, P., and Teller, E., in J. Am. Chem. Soc. Vol. 60, pp 309–16, (1938).

The term "low surface area" is used to characterize a carrier having a surface area of no more than about 10 square meters per gram, preferably in the range of from about 0.001 to about 10 square meters per gram, and most preferably from about 0.01 to about 5 square meters per gram.

Typical of such carriers which may be employed in the process of this invention are alpha-alumina, silicon carbide, and zirconia and the like, but it is preferably composed of an aggregate of alpha-alumina particles, which may be fused together or cemented together with, for example, silica or baryta.

In most cases the preferred carrier will most likely be alpha-alumina, such as described in the patent literature: see for example, U.S. Pat. Nos. 2,294,383; 3,172,893; 3,332,887; 3,423,328; and 3,563,914.

The alpha-alumina support employed to date are conventional in their chemical composition and crystalline structure. Their physical characteristics lie within the aforementioned parameters. In particular, the porosity of the support may be between about 0.1 cubic centimeter per gram and about 0.8 cubic centimeter per gram of support and, preferably between about 0.2 cubic centimeter per gram and about 0.6 cubic centimeter per gram; the surface area may be between about 0.3 square meter per gram and about 10 square meters per gram of alpha-alumina support and, preferably, about 0.6 square meter per gram to 8 square meters per gram; and the average pore size of the pores in the support may be between about 0.05 micron to about 200 microns, a major proportion of the pores having a size in the range of between about 0.05 micron to about 200 microns, the preferred average pore size being between about 0.1 micron to about 60 microns or greater.

The metallic palladium or salt thereof that is deposited on the carrier is typically in the form of small particles. The particle size of the deposited metallic palladium or salt thereof and the relative dispersion of the particles are usually important in the performance of the catalyst. The greater the dispersion, generally, the more the production rate is enhanced. The actual dispersion of the particles on the carrier is believed to be related to the surface characteristics of the carrier.

The deposition of palladium or salt thereof onto the carrier can be achieved by a number of techniques but the two techniques which are frequently employed involve, in one case, the impregnation of the carrier with a palladium solution followed by heat treatment of the impregnated carrier to effect deposition of the palladium on the carrier and, in the other case, the coating of the palladium on the support by the preformation of palladium into a slurry such that the palladium particle are deposited on the carrier and adhere to the carrier surface when the carrier is heated to remove the liquids present. These various procedures are exemplified in various U.S. Pat. Nos. such as 2,773,844; 3,207,700; 3,501,407; 3,664,970 (see British Patent Nos. 754,593); and 3,172,893.

The surface area provided by the carrier has been the subject of considerable interest in the development of various catalysts. Disclosures concerning the surface area of such classes of catalyst carriers can be found in U.S. Pat. No. 2,766,261 (which discloses that a surface area of 0.002-10 square meters per gram is suitable); U.S. Pat. No. 3,172,893 (which depicts a porosity of 35-65 percent and a pore diameter of 80-200 microns); U.S. Pat. No. 3,725,307 (which depicts a surface area of less than 1 square meter per gram and an average pore diameter of 10-15 microns); U.S. Pat. No. 3,664,970 (which utilizes a support having a minimum porosity of about 30 percent at least 90 percent of the pores having diameters in the range of 1-30 microns, and the average of such diameters being in the range of 4-10 microns); and U.S. Pat. No. 3,563,914 (which utilizes a catalyst support having a surface area of less than 1 square meters per gram, a volume of 0.23 ml/gm and a particle size between 0.074 and 0.30 mm.).

U.S. Pat. No. 4,038,175 discloses a hydrogenation process which employs palladium or platinum metal dispersed on the surface of an alpha-alumina support. The description beginning at column 3, line 42 to column 4, line 24, and the description at column 5, line 2 to column 8, line 22, relating to the description of alpha-alumina and the process for preparing the catalyst disclosed therein is incorporated herein by reference because such can be employed in practicing this invention.

CARRIER SELECTION

The chemical composition of the carrier is not narrowly critical. Alpha-alumina based carriers are highly preferred. The most preferred alpha-alumina carriers are of very high purity, i.e., at least 80 wt. percent alpha-alumina, the balance being a mixture of silicon dioxide, various alkali oxides, alkaline earth oxides, iron oxide, and other metal and non-metal oxides. Alpha-alumina carriers having a purity of at least about 98 weight percent are highly desirable in practicing this invention, the remaining components being silica, alkali metal oxide (e.g. sodium oxide) and trace amounts of other metal and non-metal impurities. A wide variety of such carriers are commerically available. The carriers are particulate and desirably are shaped in the form of pellets, extruded particles, spheres, rings, cylindrical rings and the like. The size of the carriers may vary from about 1/16" to ½". The carrier size is chosen to be consistent with the type of reactor employed. In general, for fixed bed reactor applications, sizes in the range of ⅛" to 3/8" should be suitable in the typical tubular reactor used in commercial operations. Monolith carriers may be found to be advantageous owing to their heat transfer characteristics.

CATALYST PREPARATION

A variety of procedures may be employed for preparing the palladium catalysts for use in accordance with the present invention. Typical of these procedures are those disclosed in U.S. Pat. No. 4,038,175.

The two most common procedures are: (1) impregnating a porous catalyst carrier with a solution comprising a solvent or solubilizing agent, palladium salt in an amount sufficient to deposit the desired weight of palladium upon the carrier, and thereafter, if desired, treating the impregnated carrier to convert at least a fraction of the palladium salt to palladium metal on the carrier surface; or (2) coat the palladium onto the carrier from an emulsion or slurry containing the same followed by heating the carrier as described above. Impregnation of the carrier is generally the preferred technique for palladium deposition because palladium is utilized more efficiently than by coating procedures, the latter being generally unable to effect substantial palladium deposition onto the interior surfaces of the carrier. In addition, coated catalysts are more susceptible to palladium loss by mechanical abrasion.

The palladium solution used to impregnate the carrier generally comprises a palladium salt or complex in a solvent or complexing/solubilizing agent. The particular palladium salt or complex employed is not critical and may be chosen, for example, from among palladium nitrates, sulfates, halides, phosphates, carboxylates, such as palladium acetate, benzoate, oxalate, citrate, phthalate, lactate, propionate, butyrate and higher fatty acid salts, or palladium acetylacetonate and the like. Although any palladium salt may be used to prepare the palladium catalyst employed in the process of this invention the catalyst is preferably prepared such that the catalyst is substantially free of halogen, especially chloride, and sulfur. The presence of such halogen or sulfur atoms may interfere with the formation of the diester of oxalic acid. In addition, the presence of halogen or sulfur atoms may result in increased production of deleterious by-products such as carbonates, formate and the like with the resulting loss in yield of the oxalic acid diester. Thus, the concentration of halogen or sulfur atom is preferably less than about 10 ppm, by weight, based on the palladium deposited on the carrier.

The amount of palladium deposited on the carrier is not narrowly critical and is in the range of from about 0.001 to about 10 percent by weight, preferably 1 from about 0.01 to about 5 percent by weight and most preferably from about 0.1 to about 2 percent by weight, calculated as metallic palladium.

Following impregnation of the catalyst carrier with palladium or a salt thereof, the impregnated carrier particles are separated from any remaining nonabsorbed solution or slurry. This is conveniently accomplished by draining the excess impregnating medium or alternatively by using separation techniques, such as, filtration or centrifugation. The impregnated carrier is then generally heat treated (e.g., roasted) to effect, if desired, decomposition and reduction of the palladium salts to metallic palladium, such heating is preferably carried out in air, nitrogen, hydrogen or carbon dioxide atmospheres or a combination of them. The equipment used for such heat treatment may use a static or flowing atmosphere of such gases to effect reduction.

A typical alpha-alumina carrier which may be employed in practicing the invention is one having the following chemical composition and physical properties and for reference herein is designate as Carrier "A":

|  | Wt. Percent |
|---|---|
| Chemical Composition of Carrier "A" | |
| Alpha-Alumina | 98.5 |
| Silicon Dioxide | 0.74 |
| Calcium Oxide | 0.22 |
| Sodium Oxide | 0.16 |
| Ferric Oxide | 0.14 |
| Potassium Oxide | 0.04 |
| Magnesium Oxide | 0.03 |
| Physical Properties of Carrier "A" | |
| Surface Area[1] | ~0.3 m$^2$/g |
| Pore Volume[2] (or water absorption) | ~0.05 cc/g |
| Packing Density[3] | 0.70 g/ml |
| Median Pore Diameter[4] | 21 microns |

| Pore Size Distribution, Percent Total Pore Volume[4] | |
|---|---|
| Pore Size, Microns | TPV (Percent) |
| 0.1–1.0 | 1.5 |
| 1.0–10.0 | 38.5 |
| 10.0–30.0 | 20.0 |
| 30–100 | 32.0 |
| >100 | 8.0 |

[1]Method of measurement described in "Absorption, Surface Area and Porosity", S. J. Gregg and K. S. W. Sing, Academic Press (1967), pages 316–321.
[2]Method of Measurement as described in ASTM C20-46.
[3]Calculated value based on conventional measurement of the weight of the carrier in a known volume container.
[4]Method of measurement described in "Application of Mercury Penetration to Materials Analysis", C. Orr Jr., Powder Technology, Vol. 3, pp. 117–123 (1970).

The solution used for impregnating the carrier is prepared at a concentration such that the finished catalyst contains the desired amounts of palladium. The required concentration of palladium in solution for the given carrier is calculated from the packing density (grams/cc) and pore volume of the carrier which are either known or readily determined. Assuming that all of the palladium in the impregnating solution is deposited upon the carrier, the amount of palladium required in the solution may be calculated such that between about 0.001 and 10 percent palladium is provided on the carrier.

The particle size of palladium metal or salt thereof deposited upon the carrier and the dispersion of the palladium are a function of the catalyst preparation procedure employed. Thus, the particular choice of solvent and/or complexing agent, palladium salt, heat treatment conditions and catalyst carrier may affect, to varying degrees, the size of the resulting palladium particle. For carriers of general interest for the production of diesters of oxalic acid, a distribution of palladium particle sizes below about 10,000 Angstroms is preferred. However, the role of particle size and dispersion of the palladium upon the effectiveness of the catalyst in making the diesters of oxalic acid is not clearly understood. In view of the fact that the palladium particles may migrate on the surface of the catalyst when used in the catalyic reaction resulting in a marked change in their size and shape, palladium particle size may or may not be a significant factor in affecting catalytic performance. A high dispersion of palladium is considered to be preferred.

The process of this invention is further illustrated by the following examples. These examples are provided solely to illustrate the invention and are not, in any way, to be construed as limiting.

EXPERIMENTAL PROCEDURE

The following examples were carried out in a tubular reactor formed of a 4 feet long by 1 inch (inside diameter) stainless steel tube and operated in a downflow configuration. The top (inlet) of the reactor is packed with glass beads to act as a preheating zone for the mixture of alkyl nitrite, (inert gaseous diluent) and carbon monoxide prior to introduction to the catalyst bed. The catalyst bed was formed of 10 cc of a supported palladium catalyst (as designated in each example) held in place by a thin porous glass wool plug. The tubular reactor was within a liquid containing jacket which was wrapped with electrical resistance heaters to provide even heating. The temperature of the catalyst bed was measured by a thermocouple placed therein. The alkyl nitrite was introduced by passing a CO/N$_2$ mixture through liquid alkyl nitrite (saturator) to provide a gaseous stream with CO, N$_2$ and alkyl nitrite in the vapor state.

EXAMPLES 1–6

The following catalyst preparation procedures were carried out for the catalysts employed in examples 1–6:

The catalyst employed in examples 1–6 was prepared with Norton LA 4102 alpha-alumina (U.S. Standard 8–20 mesh) as the carrier having the following chemical and physical properties:

|  | Wt. Percent |
|---|---|
| Chemical Compositions | |
| Alpha-Alumina | 99.6 |
| Silicon Dioxide | 0.01 |
| Calcium Oxide | 0.07 |
| Sodium Oxide | 0.21 |
| Ferric Oxide | 0.05 |
| Potassium Oxide | 0.03 |
| Magnesium Oxide | 0.01 |
| Physical Properties | |
| Surface Area | ~1.0 m$^2$/g |
| Apparent Porosity (1%) | ~50–56 |
| Bulk Density (g/cc) | 1.7–2.0 |
| Packing Density (lbs/ft$^3$) | 67–73 |

The catalyst was prepared by placing 800 gm of crushed (with a mortar and pestle) Norton LA 4102 carrier into a round-bottom flask and heating to about 60° C. under vacuum using heat lamps. Pd(acac)* (11.45 grams) was dissolved in 280 cc of toluene at 70° C. and the hot solution was added to the hot alumina particles through a syringe while shaking the flask. The resulting mixture was allowed to stand for 30 minutes and then transferred to an open dish. In an oven with N$_2$ flowing through it, the catalyst was heated at 85° C. for one hour, at 110° C. for two hours and finally at 150° C. for two hours before cooling to room temperature. The catalyst was then placed in a quartz tube and heated to 500° C. over a 45-minute period under a 50/50 mixture (by volume) of nitrogen and air. Flows are generally about 200 cc/min. The catalyst was then heated at 500° C. for 3 hrs. under 100° /° air and then for 15 minutes with 100% N$_2$. This was followed by 3 hrs. at 500° C.

*Pd(acac) is palladium acetylacetonate under 100% $H_2$ after which time it was cooled to 80° C. under 100% $N_2$ and cooled to room temperature.

The process parameters and the results of examples 1-6 are set forth in Table I.

COMPARATIVE EXAMPLES 7-12

Examples 7-12 were carried out to compare the results of examples 1-6 with results obtained using catalysts prepared with carriers having high surface areas, i.e. surface areas greater than 10 square meters per gram.

The catalysts employed in examples 7 and 8 were prepared using Columbia (TM) carbon (from Union Carbide Corporation) as the carrier having the following properties:

| Property | Value |
| --- | --- |
| Surface Area (m²/g) | ~1000 |
| Moisture³ (% Max) | 2.0 |
| Activity¹ (% min) | .05 |
| Hardness⁵ (min) | 90 |
| Ash⁴ (% max) | 2.0 |
| Density² (grms/cc, max) | .51 |

¹Carbon Tetrachloride Activity is the percent by weight of carbon tetrachloride absorbed at 35° C. from dry air saturated with this vapor at 0° C. (This value can be used as a relative indication of the adsorptive capacity of activated carbons).
²Density is the maximum weight per unit volume that can be contained in a given vessel.
³Moisture content as the percentage loss in weight of a sample after heating for 6 hours at 150° C.
⁴Total Ash represents the weight percent of residue remaining after burning in air at 500° C.
⁵Hardness is a measure of the ability of the carbon sample to resist mechanical breakdown. Hardness numbers are expressed as percent average particle diameter remaining after a period of mechanical agitation with steel balls.

The catalyst employed in example 7 was prepared by placing 10 grams of carbon carrier in a round bottom flask heated with heat lamps under vacuum; then 0.429 grams of Pd(acac)2 was dissolved in 12 cc of hot toluene (70° C.) and the resulting solution was added via syringe to the carbon while shaking the flask. The resulting material was heated in an open dish in the hood at 85° C. for one hour and then for two hours at 115° C. The catalyst was then placed in a quartz tube and treated sequentially as follows: (Gas flows are generally about 200 cc/min.)

1. 350° C. under 50/50 $H_2$/air over a 30 min. period and then hold at 350° C. for 30 more min.;
2. 350° C. for four hrs., under 100% air; and
3. 350° C. for 30 min. under 100% $N_2$ flow and then cooled to room temperature.

The catalyst employed in example 8 was prepared by placing ten grams of the aforementioned carbon carrier in a round-bottom flask under vacuum at room temperature. Then, 0.250 grams of $PdCl_2$ was dissolved in a mixture of 6.0 cc distilled water and 6.0 cc of concentrated hydrochloric acid at 40° C. The solution was added to the carbon through a syringe while shaking the flask and then placed in an open dish at 85° C. The solution was added to the carbon through a syringe while shaking the flask and then placed in an open dish at 85° C. for one hour, 115° C. for two hours, 150° C. for two hours and then 200° C. for an additional two hours. The catalyst was then placed in a quartz tube and treated sequentially as follows: (Gas flows are generally about 200 cc/min.)

1. 350° C. over a one-hour period under 50:50 $N_2/H_2$ and then hold at 350° C. for one hour;
2. 350° C. for four hours with 100% air; and
3. cooled to 80° C. and under 100% $N_2$ and cooled to room temperature.

The process parameters and the results of comparative examples 7-12 are set forth in Table 11.

TABLE I(8)

| Example(1) | CO (%)(2) | Temperature (°C.) | Flow Rate (cc/mm) | Reaction Time (hr) | Feed(4) | Nitrite Conversion % | Oxalate Rate(6) | Efficiency(7) % |
| --- | --- | --- | --- | --- | --- | --- | --- | --- |
| 1(3) | 25 | 117 | 300 | 5.0 | 19.0 | 92 | 1.8 | 76 |
| 2 | 25 | 117 | 600 | 6.0 | 52.3 | 87 | 4.1(5) | 81 |
| 3 | 25 | 119 | 800 | 5.5 | 51.0 | 81 | 4.2 | 84 |
| 4 | 25 | 123 | 1000 | 4.5 | 59.5 | 72 | 5.7 | 89 |
| 5 | 50 | 117 | 600 | 5.0 | 44.0 | 60 | 3.1 | 87 |
| 6 | 22 | 118 | 600 | 5.5 | 44.8 | 75 | 3.65 | 92 |

(1)A single 10 cubic centimeter catalyst charge was employed in each example and comprised 0.5 percent by weight Pd on an alpha-alumina carrier. Ethyl nitrite was selected as the ester of nitrous acid in each example.
(2)In the CO/$N_2$ mixture fed to the alkyl nitrite saturator.
(3)Example 1 is the first experiment conducted with the particular catalyst employed therein. Effeciency may have been affected by initial surface characteristics of the catalyst employed therein.
(4)Total grams of nitrite provided over the reaction period.
(5)It is believed that a higher than expected nitrite concentration was present in this example thereby resulting in an artificially higher rate. When normalized it is believed that the rate is about 3.3 gram moles liter-catlyst⁻¹ hour⁻¹.
(6)grams-moles liter-catalyst⁻¹ hour⁻¹.
(7)Efficiency based on amount of alkyl nitrite converted to products.
(8)Examples 1-6 were carried out under superatmospheric pressure.

TABLE II(11)

| Example | CO (%)(7) | Temperature (°C.) | Flow Rate (cc/mm) | Reaction Time (hr) | Feed(8) | Nitrite Conversion % | Oxalate Rate(9) | Efficiency(10) % |
| --- | --- | --- | --- | --- | --- | --- | --- | --- |
| 7(1) | 25 | 109 | 600 | 3.0 | 20.9 | 75 | 2.6 | 76 |
| 8(2) | 25 | 106 | 600 | 4.5 | 36.0 | 83 | 1.6 | 35 |
| 9(3) | 25 | 107 | 600 | 2.0 | 20.3 | 10 | 0.4 | 50 |
| 10(4) | 25 | 114 | 300 | 3.0 | 9.8 | 66 | 1.1 | 75 |
| 11(5) | 25 | 118 | 300 | 6.0 | 22.9 | 90 | 1.5 | 65 |

TABLE II[11]-continued

| Example | CO (%)[7] | Temperature (°C.) | Flow Rate (cc/mm) | Reaction Time (hr) | Feed[8] | Nitrite Conversion % | Oxalate Rate[9] | Efficiency[10] % |
|---|---|---|---|---|---|---|---|---|
| 12[6] | 25 | 115 | 600 | 3.5 | 24.5 | 75 | 2.7 | 78 |

[1]1.5 percent by weight Pd formed with Pd(acac)$_2$ on carbon.
[2]1.5 percent Pd by weight formed with PdCl$_2$ on carbon; X-ray analysis indicated residual chlorine present.
[3]1.5 percent Pd by weight on pelletized carbon from Ventron, 152 Andover Steet, Danvers, Ma. 01923, X-ray analysis indicated sulfur was present.
[4]0.5 percent Pd by weight on carbon from Calsicat (TM) Division of Mallinkrodt, 1707 Gaskell Avenue, Erie, Pa. 16503.
[5]0.5 percent Pd by weight on carbon from Engelhard Mineral and Chemical Corporation, 429 Delancy Street, Neward, N.J. 07105.
[6]0.5 percent Pd by weight on gamma-alumina from Alfa Products, Thiokol/Ventron Division, 152 Andover Steet, Danvers, Ma. 01923.
[7]In the CO/N$_2$ mixture fed to the alkyl nitrite saturator.
[8]Total grams of nitrite (ethyl nitrite was employed in each example) provided over the reacton period).
[9]gram-moles/liter-catalyst$^{-1}$ hour$^{-1}$.
[10]Efficiency based on amount of alkyl nitrite converted to products.
[11]Examples 7-12 were carried out under superatmospheric pressure.

What is claimed is:

1. The vapor phase heterogeneous process for preparing a diester of oxalic acid which comprises contacting a vaporous ester of nitrous acid with carbon monoxide in the vapor state in the presence of a solid palladium supported catalyst comprising metallic palladium or a salt thereof deposited on a non-acidic, alpha alumina carrier having a surface area between about 0.001 and 10 square meters per gram at a temperature of between about 50° C. and about 200° C., wherein such ester of nitrous acid is formed by reaction of a nitrogen compound with a saturated aliphatic monohydric alcohol and recovering a diester of oxalic acid, in which the ester group corresponds to the alcohol formed in making the ester of nitrous acid.

* * * * *

UNITED STATES PATENT AND TRADEMARK OFFICE
CERTIFICATE OF CORRECTION

PATENT NO. : 4,616,093

DATED : October 7, 1986

INVENTOR(S) : L. A. Kapicak and J. P. Henry

It is certified that error appears in the above-identified patent and that said Letters Patent is hereby corrected as shown below:

Column 2, line 4, between "oxalic" and "nitrous" insert --acid which comprises contacting a vaporous alkyl ester of--.

Column 6, line 57, delete "1".

Column 7, Table, Pore Volume, delete "0.05" and insert therefor --0.50--.

Column 8, line 67, delete "100° /°" and insert therefor --100%--.

Column 9, line 1, "Pd(acac ... acetylacetonate" should be shown as a footnote. The balance of the sentence "under ... temperature." should be shown as text.

Column 11, Table II, Footnote (8), delete final parenthesis.

Signed and Sealed this

Twenty-second Day of March, 1988

*Attest:*

DONALD J. QUIGG

*Attesting Officer*  *Commissioner of Patents and Trademarks*